US011185707B2

(12) United States Patent
Halperin et al.

(10) Patent No.: US 11,185,707 B2
(45) Date of Patent: Nov. 30, 2021

(54) MRI-COMPATIBLE CARDIAC DEFIBRILLATOR

(71) Applicant: The Johns Hopkins University, Baltimore, MD (US)

(72) Inventors: Henry Halperin, Baltimore, MD (US); Ehud J. Schmidt, Boston, MA (US); Ronald D. Watkins, Stanford, CA (US); Harikrishna Tandri, Ellicott City, MD (US); David Hunter, Baltimore, MD (US); Leslie Tung, Columbia, MD (US); Ronald D. Berger, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 181 days.

(21) Appl. No.: 16/467,373

(22) PCT Filed: Dec. 8, 2017

(86) PCT No.: PCT/US2017/065441
§ 371 (c)(1),
(2) Date: Jun. 6, 2019

(87) PCT Pub. No.: WO2018/107106
PCT Pub. Date: Jun. 14, 2018

(65) Prior Publication Data
US 2020/0086130 A1    Mar. 19, 2020

Related U.S. Application Data

(60) Provisional application No. 62/432,079, filed on Dec. 9, 2016.

(51) Int. Cl.
*A61N 1/39* (2006.01)
*A61B 5/055* (2006.01)
*A61B 5/361* (2021.01)

(52) U.S. Cl.
CPC .......... *A61N 1/3904* (2017.08); *A61B 5/055* (2013.01); *A61N 1/3925* (2013.01); *A61B 5/361* (2021.01)

(58) Field of Classification Search
CPC ..... A61N 1/3925; A61N 1/3904; A61B 5/055
See application file for complete search history.

(56) References Cited

U.S. PATENT DOCUMENTS

| 7,643,876 | B2 * | 1/2010 | Zhang | A61N 1/36071 607/5 |
| 8,521,300 | B2 * | 8/2013 | Makdissi | A61N 1/3718 607/62 |

(Continued)

OTHER PUBLICATIONS

International Search Report from corresponding International Application No. PCT/US2017/065441, dated Mar. 29, 2018.

(Continued)

*Primary Examiner* — William J Levicky
*Assistant Examiner* — Michael A Rizzuto
(74) *Attorney, Agent, or Firm* — Venable LLP; Henry J. Daley; Aziz H. Poonawalla

(57) ABSTRACT

A magnetic-resonance-imaging-compatible (MRI-compatible) cardiac defibrillator includes: a defibrillator generator; first and second electric wires, each being electrically connected to said defibrillator generator; first and second defibrillation pads, each being electrically connected to a respective one of said first and second electric wires; and a low pass filter electrically connected between said defibrillator generator and said first and second electric wires to prevent a noise in an MRI image caused by a radiofrequency interference from the defibrillator as well as protect a patient and the defibrillator from MRI radiofrequency imaging signals, wherein said low pass filter has a cutoff frequency set such that differential mode noise at an MRI Larmor frequency is in an attenuated band while a system-test signal (Continued)

by said defibrillator generator is in a pass band of said low pass filter.

16 Claims, 9 Drawing Sheets

(56) References Cited

U.S. PATENT DOCUMENTS

| | | | |
|---|---|---|---|
| 8,600,519 B2 | 12/2013 | Stevenson et al. | |
| 2008/0243218 A1* | 10/2008 | Bottomley | A61N 1/05 607/116 |
| 2010/0023000 A1* | 1/2010 | Stevenson | A61B 18/1492 606/33 |
| 2013/0141093 A1* | 6/2013 | Lang | A61B 5/259 324/309 |

OTHER PUBLICATIONS

Written Opinion from corresponding International Application No. PCT/US2017/065441, dated Mar. 29, 2018.

Schmidt et al., "An MRI-compatible defibrillator: initial testing in volunteers and swine", Journal of Cardiovascular Magnetic Resonance, Jan. 2016, vol. 18 (Suppl 1), Article No. 0122, pp. 1-2.

Schmidt et al., "A magnetic resonance imaging-conditional external cardiac defibrillator for resuscitation within magnetic resonance imaging scanner bore", Circulation: Cardiovascular imaging, Oct. 2016, vol. 9, Issue 10, Article No. e005091, pp. 1-9.

* cited by examiner

System Layout in 1.5 Tesla MRI Suite

Generator display during cardiac arrest

Generator display during early recovery

MRI-COMPATIBLE CARDIAC DEFIBRILLATOR

This application is a National Stage Application under 35 U.S.C. § 371 of International Application No. PCT/US2017/065441, filed Dec. 8, 2017, which claims priority to U.S. Provisional Application No. 62/432,079, filed on Dec. 9, 2016, the entire contents of which are hereby incorporated herein by reference. All references cited anywhere in this specification, including the Background and Detailed Description sections, are incorporated by reference as if each had been individually incorporated.

This invention was made with Government support under Grant Nos. U41-RR019703, AHA 10SDG261039, R03 EB013873-01, U54-111,119145, and R01-HL094610 awarded by the National Institutes of Health (NIH). The Government has certain rights in the invention.

BACKGROUND

1. Technical Field

The field of the currently claimed embodiments of this invention relates to MRI-compatible cardiac defibrillators and kits for converting a cardiac defibrillator to an MRI-compatible cardiac defibrillator.

2. Discussion of Related Art

Magnetic resonance imaging (MRI) is a diagnostic exam that generally uses a combination of a large magnet, radiofrequencies and a computer to produce detailed images of organs and structures within the body. MRI has emerged as the premier imaging modality for the evaluation of a multitude of diseases. In brain, spine and joint imaging, MRI is the modality of choice for the diagnosis of both degenerative and malignant disease, a result of the multitude of available imaging contrasts (T1-weighted, T2-weighted, magnetic susceptibility-weighted [T2*-weighted], oxygenation [Blood-Oxygen-Level-Dependent (BOLD)], diffusion-weighted, contrast-perfusion, non-contrast perfusion) that provide for superior inter-tissue contrast. While MRI was initially restricted to non-trauma, and non-emergency, applications, it has become the method of choice for the diagnosis of several trauma conditions, such as acute ischemic stroke, acute spinal trauma and acute joint disease, leading to MRI-scanner installation in many emergency rooms.

In the cardiovascular system, MRI has long played an important role in vascular imaging, as well as for the diagnosis of several focal and diffuse diseases of the myocardium. It is also extensively used for the assessment of chronic ischemic disease, as a result of the powerful contrasts provided by Late Gadolinium Enhancement (scar imaging), T2-weighted (edema imaging) and strain (mechanical function imaging). In recent years, MRI has been shown to be important for the diagnosis of sub-acute ischemia, leading to an increase in MRI-based pharmacological stress tests. MRI has also been shown to be a valuable differentiator between chronic and acute infarcts, so its use in emergency-room cardiology may grow as well.

The field of MRI-guided surgical intervention is also continuously growing. MRI-guided biopsy, excision and ablation of head, spine, abdominal and pelvic tumors is performed at hundreds of sites world-wide. In the cardiovascular system, MRI imaging is routinely used for pre-operative mapping before catheter-based interventions in the heart, such as for the treatment of arrhythmia (atrial fibrillation and ventricular tachycardia). Intra-operative MRI guidance during electro-physiological (EP) mapping and ablative procedures has been performed in animal models for the past 15 years. These animal EP procedures have shown that MRI methods can detect the causes for arrhythmia recurrence post-procedure. As a result, human trials are on-going to test the feasibility of intra-procedural MRI use during EP ablative procedures.

However, there are large patient populations that are excluded from MRI-imaging and MRI-guided intervention. Patients which are hemodynamically unstable (irregular heart rate, elevated blood pressure), have a history of sub-acute to acute ischemia, have implanted devices, or suffer from heart failure, have counter-indications that lead to their exclusion from most MRI imaging studies and MRI-guided interventions. Excluded procedures include those where the advantages of MRI are well-known; acute stroke imaging, MR angiography, brain tumor excision, abdominal tumor ablation, as well as cardiac stress perfusion.

The major reason for the exclusions lies in the current inability to detect and intervene quickly should a cardiac event occur inside the MRI bore. For rapid detection of a cardiac event, MRI-compatible 12-lead electrocardiographic (ECG) systems are currently under development, while existing MRI-compatible monitoring systems can detect hemodynamic and oxygenation emergencies.

The ability to rapidly intervene requires accessible cardio-pulmonary resuscitation (CPR) and defibrillation systems. These are currently unavailable. Typically, a cardiac event that occurs inside the bore may include: (1) taking the patient out of the bore; (2) removing the MRI coils and transferring the patient from the MRI-table to a transport gurney [or undocking the MRI table and using it for transport]; (3) moving the patient out of the MRI suite; (4) attaching defibrillation pads; and (5) administering the defibrillation pulses. This sequence delays the administration of defibrillation by several minutes, which presents a significant risk of increased mortality. Therefore, there remains a need for MRI-compatible defibrillators to help patients undergo an MRI scan more safely.

When a defibrillator discharge is applied to a patient, there is a stimulation of the skeletal muscle of the thorax causing substantial contraction of that muscle which results in a sudden movement of the patient, often described as "jumping". This jumping inside the bore of an MRI scanner may cause injury to the patient and potential damage to the MRI scanner.

Therefore, therefore there also remains a need for reducing or eliminating such jumping to prevent injury to the patient and potential damage to the MRI scanner.

SUMMARY

According to some embodiments of the invention, a magnetic-resonance-imaging-compatible (MRI-compatible) cardiac defibrillator includes: a defibrillator generator; first and second electric wires, each being electrically connected to the defibrillator generator; first and second defibrillation pads, each being electrically connected to a respective one of the first and second electric wires; and a low pass filter electrically connected between the defibrillator generator and the first and second electric wires to prevent noise in an MRI image caused by radiofrequency interference from the defibrillator, as well as protect a patient and the defibrillator from MRI radiofrequency imaging signals, wherein the low pass filter has a cutoff frequency set such that differential mode noise at an MRI Larmor frequency is in an attenuated band while a system-test signal by the defibrillator generator is in a pass band of the low pass filter.

According to some embodiments of the invention, a kit for converting a cardiac defibrillator to an MRI-compatible cardiac defibrillator is provided and the cardiac defibrillator includes a defibrillator generator. The kit includes a low pass filter structured to be electrically connected to the defibrillator generator between first and second electric wires of the MRI-compatible cardiac defibrillator to prevent a noise in an MRI image caused by a radiofrequency interference from the defibrillator, as well as protect a patient and the defibrillator from MRI radiofrequency imaging signals, wherein the low pass filter has a cutoff frequency between a pass and attenuated bands set such that differential mode noise at an MRI Larmor frequency is in the attenuated band while a signal by the defibrillator generator for system tests is in the pass band of the low pass filter.

BRIEF DESCRIPTION OF THE DRAWINGS

The present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Figure 1A:
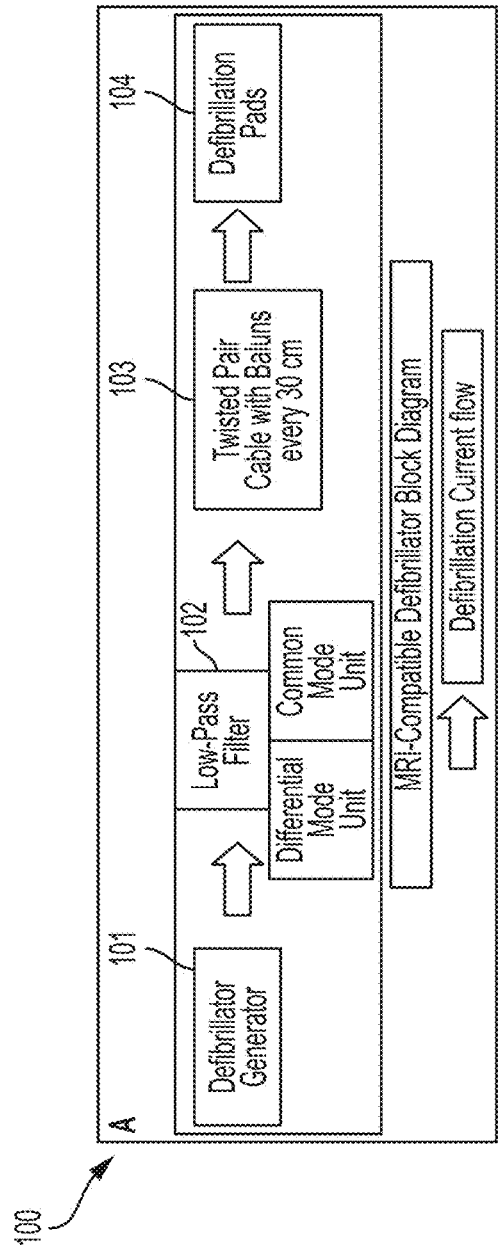
FIG. 1A shows a block diagram a MRI-compatible defibrillation system according to some embodiments of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Accordingly, some embodiments of the current invention provide an external defibrillation system for use in the MRI suite. The system is intended to be attached to patients while they are within the bore, enabling the immediate administration of defibrillation within the MRI bore.

A cardiac defibrillator system according to some embodiments of the current invention (1) can properly function inside the MRI bore, and (2) can be attached to a subject before they are placed inside the MRI, so it can be used immediately if a cardiac event occurs inside the MRI, while not compromising the performance (signal to noise) of the MRI scanner during imaging.

In some embodiments, a number of subsystems can be added to a commercial, regulatory-approved, defibrillator. These subsystems are connected (placed) between the generator and the defibrillation pads, which are positioned on the patient's chest (and thereby deliver the electrical shock to the patient's heart). The defibrillator generator itself is not modified in this embodiment and retains all of its functionality.

As a result of the fact that the generator itself is not modified, it is felt that (a) obtaining regulatory approval for this system can be obtained at a faster pace and (b) the invention can be used by multiple manufacturers of this equipment. However, the general concepts of the current invention are not limited to only this embodiment.

An example of this system has been designed, constructed and validated inside a 1.5T Tesla MRI at JHU. It has been (1) attached during human imaging, to demonstrate retention of imaging performance, and (2) used for animal defibrillation.

According to some embodiments, a magnetic-resonance-imaging-compatible (MRI-compatible) cardiac defibrillator includes: a defibrillator generator; first and second electric wires, each being electrically connected to the defibrillator generator; first and second defibrillation pads, each being electrically connected to a respective one of the first and second electric wires; and a low pass filter electrically connected between the defibrillator generator and the first and second electric wires to prevent a noise in an MRI image caused by a radiofrequency interference from the defibrillator, as well as to protect a patient and the defibrillator from MRI radiofrequency imaging signals. The low pass filter has a cutoff frequency set such that differential mode noise at an MRI Larmor frequency is in an attenuated band while a system-test signal by the defibrillator generator is in a pass band of the low pass filter.

According to some embodiments, the low pass filter is at least a 7-pole low pass filter constructed to filter the differential mode noise at the MRI Larmor frequency by at least 80 dB. According to some embodiments, the low pass filter is at least a 7-pole low pass filter constructed to filter the differential mode noise at the MRI Larmor frequency by at least 90 dB.

According to some embodiments, the first and second electric wires may be formed into a twisted pair of wires. According to some embodiments, the MRI-compatible cardiac defibrillator may further include a plurality of radiofrequency (RF) traps tuned to the MRI Larmor frequency and attached to the first and second electric wires spaced apart from each other in order to reduce common-mode emission from the defibrillator generator and to prevent patient-skin heating from RF-energy induced by an MRI scanner's body transmit coil.

According to some embodiments, the defibrillation pads may be slotted defibrillation pads. According to some embodiments, the defibrillator generator may be an MRI-compatible defibrillator generator. The MRI-compatible defibrillator generator may be substantially free of magnetic materials.

According to some embodiments, the MRI-compatible defibrillator generator may include a plurality of stages of geometric multipliers followed by a plurality stages of voltage multipliers. According to some embodiments, the MRI-compatible defibrillator generator may include six stages of geometric multipliers followed by thirteen stages of voltage multipliers.

According to some embodiments, the MRI-compatible defibrillator generator may be configured to produce a muscle-conditioning signal immediately prior to a cardiac stimulating pulse so as to decrease a degree of rapid muscle contraction by a subject undergoing cardiac defibrillation.

According to some embodiments, the MRI-compatible cardiac defibrillator may further include a non-magnetic voltage multiplier circuit for stepping up the battery and/or converting supply voltage to the voltage needed for defibrillation. According to some embodiments, the MRI-compatible cardiac defibrillator may further include a generator and switching system which applies a waveform to the patient just prior to delivery of a defibrillator shock. The waveform is used to condition the skeletal muscle to reduce or avoid its violent contraction caused by the defibrillator shock.

According to some embodiments, a kit is provided to be used for converting a cardiac defibrillator to an MRI-compatible cardiac defibrillator and the cardiac defibrillator includes a defibrillator generator. The kit may include a low pass filter structured to be electrically connected to the defibrillator generator between first and second electric wires of the MRI-compatible cardiac defibrillator to prevent a noise in an MRI image caused by a radiofrequency interference from the defibrillator, as well as protect a patient and the defibrillator from MRI radiofrequency imaging signals. The low pass filter may have a cutoff frequency between a pass and attenuated bands set such that differential mode noise at an MRI Larmor frequency is in the attenuated band while a signal by the defibrillator generator for system tests is in the pass band of the low pass filter.

According to some embodiments, the low pass filter is at least a 7-pole low pass filter constructed to filter the differential mode noise at the MRI Larmor frequency by at least 80 dB. According to some embodiments, the low pass filter may be at least a 7-pole low pass filter constructed to filter the differential mode noise at the MRI Larmor frequency by at least 90 dB. According to some embodiments, the kit may further include the first and second electric wires, and the first and second electric wires may be formed into a twisted pair of wires.

According to some embodiments, the kit may further include a plurality of RF traps tuned to the MRI Larmor frequency attached to the first and second electric wires spaced apart from each other in order to reduce common-mode emission from the defibrillator generator and to prevent patient-skin heating from RF-energy induced by an MRI scanner's body transmit coil. According to some embodiments, the kit may further include slotted defibrillation pads. According to some embodiments, the defibrillator generator is an MRI-compatible defibrillator generator.

The following describes some more details of the current invention with reference to particular experiments. The general concepts of the current invention are not limited to only the particular embodiments or experiments. Generally, there are some required specifications for the MRI-compatible defibrillation system. First, the defibrillation system is specified to perform all its diagnostic functions while inside the MRI suite and is ready for immediate administration of high-voltage (2-4 KV) defibrillation pulses, including with the subject inside the MRI scanner. This required that the defibrillation generator be present inside the MRI room, while all the associated cabling and surface pads, which supports this high-voltage administration, must be attached to the subject during their entire sojourn inside the MRI scanner. An Alternating Current (AC) system-test signal can be used to measure impedance. The frequency of the system-test signal can be in a range of 100 Hz to 1 MHz. For example, a 67 kHz system-test signal is suitable in some embodiments. Since the generator continuously tests its connection to the defibrillation pad by sending AC electric waves to the defibrillation pads and measuring their impedance (and will not fire if it detects changes in impedance), the connection at this frequency between the defibrillation generator and the defibrillation pads needed to be maintained.

Secondly, the MRI imaging performance of the scanner is specified not to be impaired by the permanent attachment of a working defibrillation system to the subject. This required that the MRI's imaging signal-to-noise ratio (SNR) not be reduced by the presence of the system. This also required that interference at the scanner's Larmor frequency be reduced to a minimum. In addition, it required that the susceptibility artifacts created by the surface pads be spatially restricted, so as not to mask important anatomy.

As per ASTM/IEC83-85 requirements related to patient safety, the cabling between the defibrillation generator and the surface pads do not increase in temperature by more than 1.5° C. during imaging which utilizes 4 Watt/kg Specific Absorption Rate (SAR) MRI sequences.

FIG. 1A shows an block diagram an MRI-compatible defibrillation system 100 according to an embodiment of the current invention. In FIG. 1A the functional flow of the system components is illustrated by horizontal arrows showing the defibrillation-current flow path.

The MRI-compatible defibrillation system 100 includes a defibrillator generator 101; a low pass filter 102; first and second electric wires 103; and first and second defibrillation pads 104. Each of the first and second defibrillation pads 104 is electrically connected to a respective first and second electric wire 103. The low pass filter 102 is electrically connected between the defibrillator generator 101 and the first and second electric wires 203.

Figure 1B:
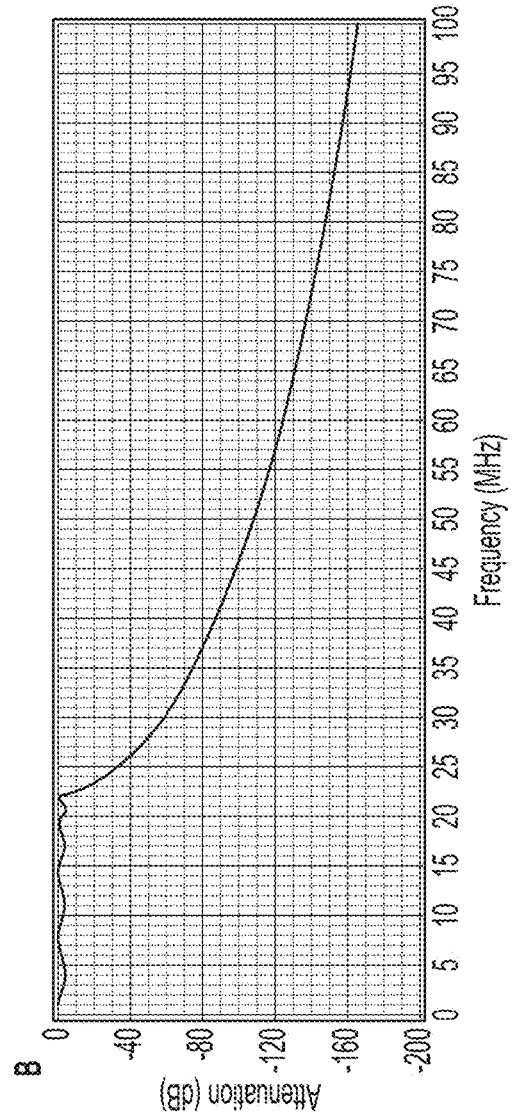
FIG. 1B shows a low-pass filter design in MRI-compatible defibrillation system according to some embodiments of the invention.

FIG. 1B shows a low-pass filter design in which the filter passes frequencies below 22 MHz and has ~120 dB attenuation at 63.8 Mhz according to one embodiment. The filter is needed to prevent a noise in an MRI image caused by a radiofrequency interference from the defibrillator, as well as protect a patient and the defibrillator from the MRI radiofrequency imaging signals. The filter is placed on the output of the generator and contains elements to remove both common-mode and differential-mode RFI emission. The filter is designed to (a) withstand the 4 KV pulses emitted during defibrillation; and (b) enable un-attenuated transmission of a sine-wave system-test signal continuously emitted by the generator to check the integrity of the connection to the surface pads. Specifically, it is designed to provide ~120 dB attenuation at 63.8 MHz, while allowing frequencies below 22 MHz to pass freely. Since the Zoll defibrillator chassis contained ferromagnetic components, it needed to be placed outside the MRI scanner's 5 Gauss magnetic-field lines, which is accommodated by its placement ~1.5 m on the side of the MRI gantry.

Figure 1C:
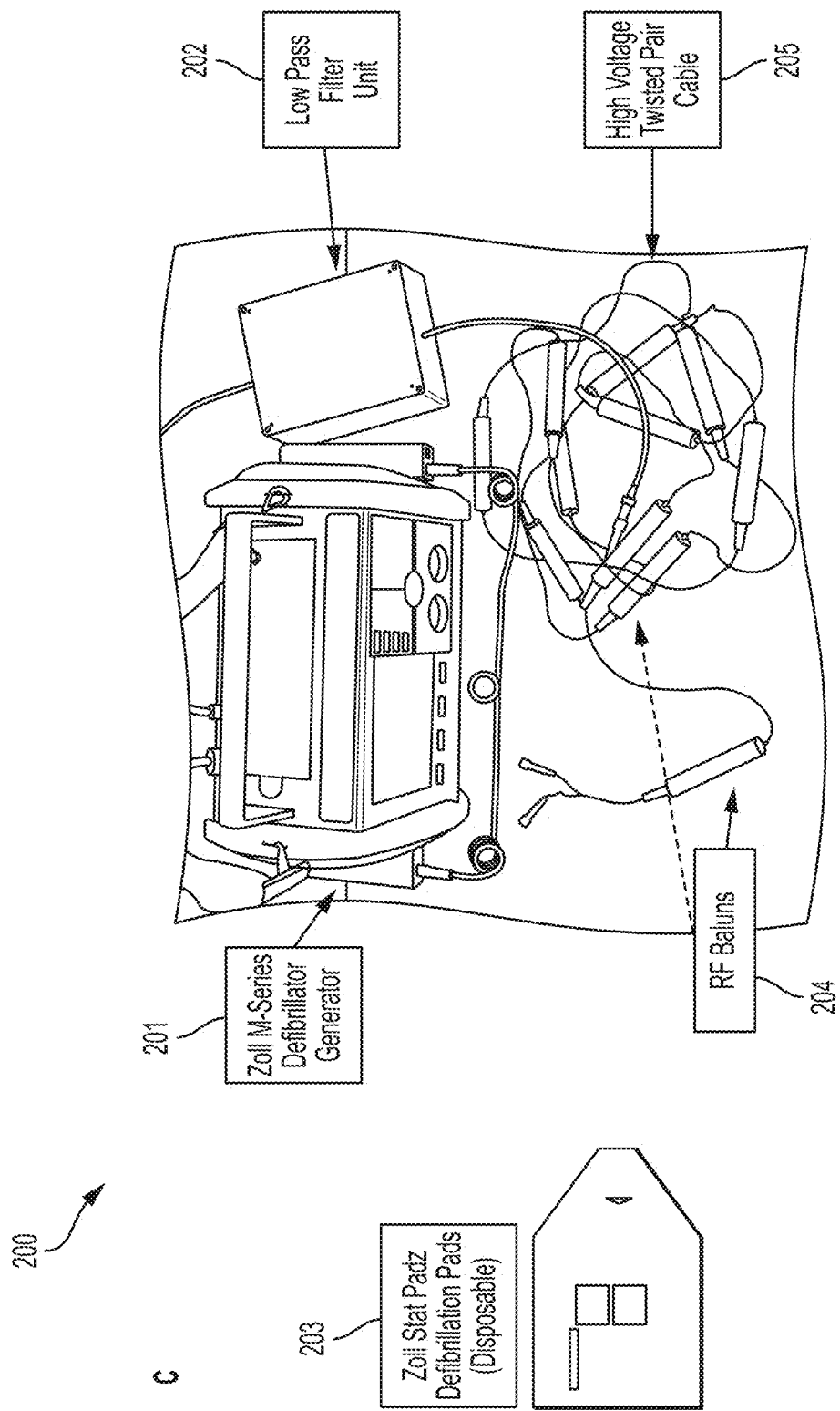
FIG. 1C shows an example of system components according to an embodiment of the current invention. The arrows point to some components of the MRI-compatible defibrillation system according to some embodiments of the invention.

FIG. 1C shows an example of system components in the MRI-compatible defibrillation system illustrated in FIG. 1A. The arrows in FIG. 1C point to key parts of the MRI-compatible defibrillation system 200. In the embodiment of FIG. 1C, the MRI-compatible defibrillation system 200 includes a defibrillator generator 201; a low pass filter 202; defibrillation pads 203; RF baluns 204, high voltage twisted pair of electric wires 205. A commercial Zoll Medical (Chelmsford, Mass.) M-Series bi-phasic defibrillation generator was used in FIG. 1C. The first and second electric wires were formed into a twisted pair of wires. Because the generator emitted large amounts of radio-frequency interference (RFI) at the MRI's operating frequency (63.8 MHz), a 9-pole low-pass filter was constructed to remove this interference. To prevent MRI-induced heating of the cables connecting the low-pass filter and the surface pads, a 4 m long twisted-pair high-voltage cable was constructed using 3 AWG gage insulated copper cable. RF traps ("Baluns") tuned to the MRI Larmor frequency were placed at 0.30 m increments along the entire cable. Their role was to attenuate waves induced by the MRI scanner's body-coil. These waves, if allowed to freely propagate, might induce temperature rises in the cable or at the surface pads. At the cable's distal end, connectors were constructed for the surface pads. A commercial Zoll Medical Stat padz multi-functional defibrillation pads (electrodes) were utilized in the FIG. 1C. The connectors of these disposable electrodes may be replaced so that they would mate with the connectors added to the distal cable, but otherwise there is no need to modify these pads.

The Study Population and Experiments Performed

Healthy volunteers (n=2) were imaged with Institutional Review Board (IRB) approval in a Siemens (Erlangen, Germany) 1.5 Tesla Avanto scanner. The volunteers were imaged using high-SAR cardiac SSFP sequences with the entire defibrillation system connected.

To test operation of the defibrillation system, a custom-built fibrillation system was utilized according to some embodiments. Using mechanical switching, the fibrillation system delivered high-voltage electrical pulses to the Zoll defibrillation pads, inducing cardiac arrest, at which point the connections were switched, disconnecting the fibrillator and connecting the defibrillator, in order to defibrillate the animals.

To assess the operation of the MRI-compatible defibrillation system, 40 kg swine models Were utilized. The swine had previously inducted chronic left-ventricular infarcts. They were anesthetized and intubated. During the experiments, the swine were fibrillated using the custom fibrillation unit (n=3), and thereafter defibrillated using the modified defibrillation system, using a 200 Joule, 8 ms pulse, biphasic pulse routine.

Two cardiac events were induced within a conventional animal fluoroscopy suite, which tested normal (non-MRI) defibrillation functionality of the modified system. Two cardiac events were then induced inside a 1.5 Tesla Siemens 0.7 m patient-bore Aera scanner. Before the cardiac arrest, during the arrest, and during the recovery to sinus rhythm which followed defibrillation, the swine were monitored using MRI-compatible hemodynamic monitors. (Invivo Precess 3160, Gainesville, Fla.)

Human Imaging Experiments

Figure 2A:
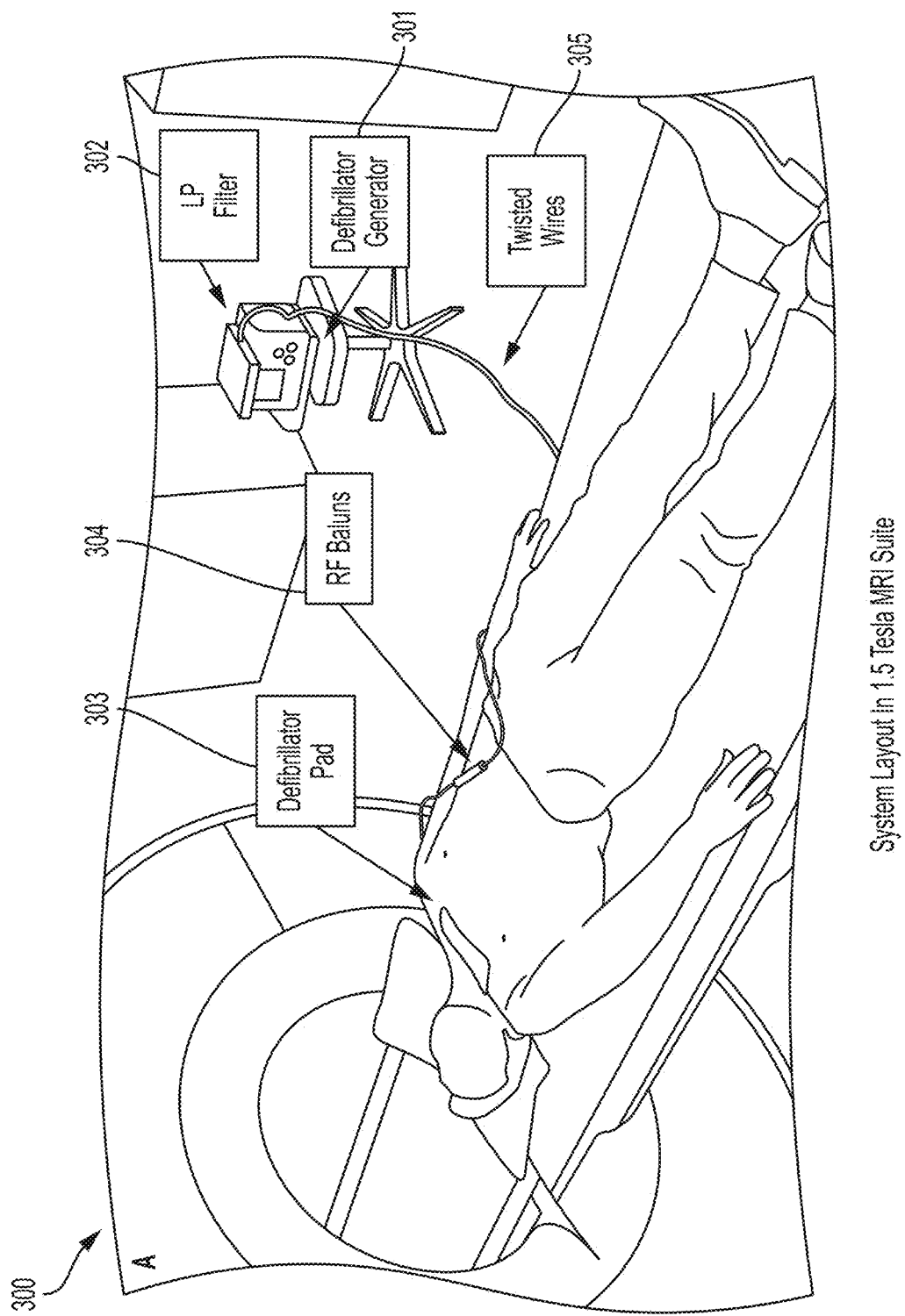
FIG. 2A shows a human test of the defibrillation system according to an embodiment of the invention.

FIG. 2A is a human test of the defibrillation system 300 according to some embodiments. The defibrillation system 300 includes a defibrillator generator 301, a low pass filter 302, defibrillation pads 303, Radio-Frequency (RF) baluns 304, and twisted pair of wires 305.

FIG. 2A shows a volunteer before being inserted into the 1.5 Tesla MRI, with heavy black arrows pointing to locations of key components of the defibrillation system 300. According on embodiment illustrated in FIG. 2A, one of the defibrillation pads 303 was placed on the middle of the volunteer's abdomen and the other on his back.

According to some embodiments, RF traps ("Baluns") 304 were tuned to the MRI Larmor frequency and placed on the defibrillation cabling at regular increments (such as 30 cm) in order to reduce common-mode emission from the defibrillator generator 301, as well as to prevent patient-skin heating from RF-energy induced by the MRI scanner's body transmit coil.

Figure 2B:
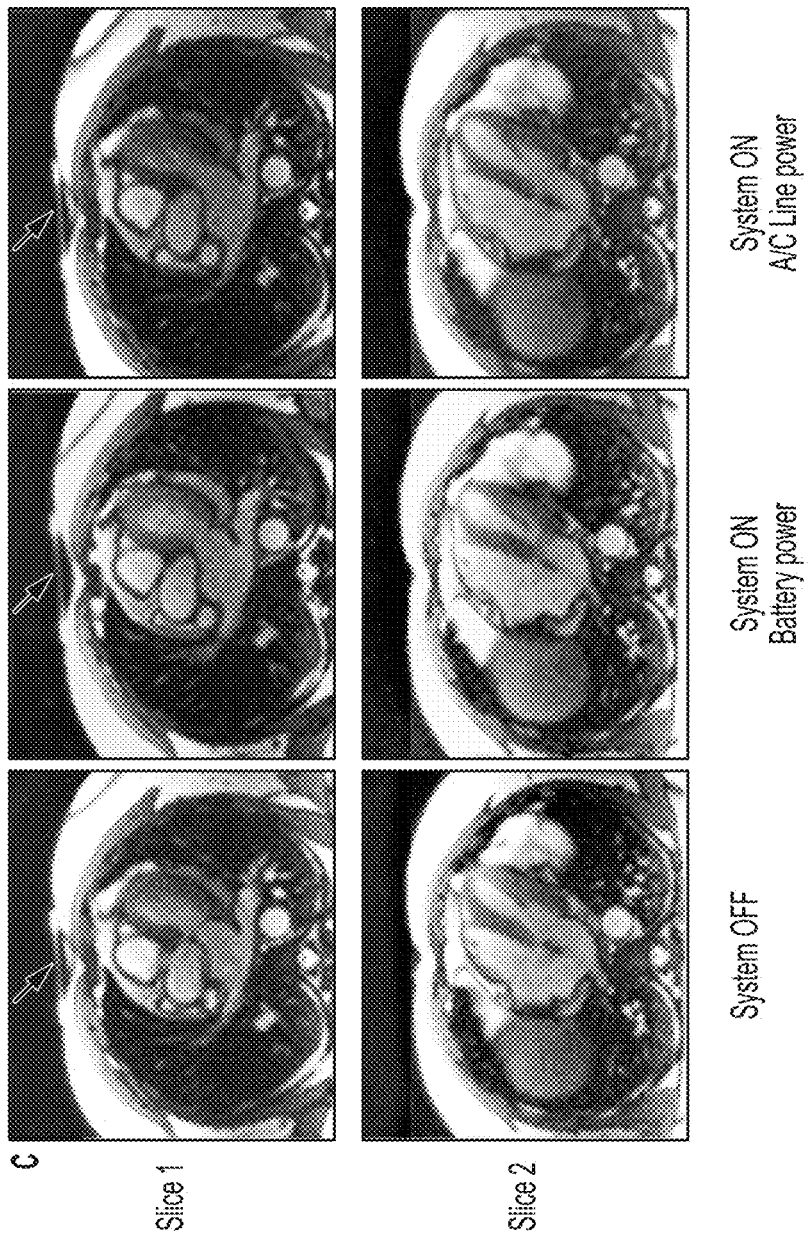
FIG. 2B shows the results of steady-state free precession (SSFP) imaging performed to assess signal-to-noise-ratio (SNR) associated with the system in FIG. 2A.

FIG. 2B shows the results of steady-state free precession (SSFP) imaging performed to assess signal-to-noise-ratio (SNR) associated with the system in FIG. 2A. To assess RFI noise levels, the Zoll Medical generator was run in three states; (a) shut-down (OFF); (b) ON and powered by its internal battery; and (C) ON and powered from a wall power outlet (A/C power) inside the MRI room. Two slices acquired at each of three different conditions are shown in FIG. 2B, with the defibrillation system shut down (left column), with the defibrillation system ON but using internal-battery supply (middle column) and with the defibrillation system ON but using A/C wall-power supply (right column). The arrows in FIG. 2B point to artifacts produced by the presence of the defibrillator pads on the subject.

Specifically, MRI Imaging SNR during SSFP imaging was measured to be $-1.6$ ($-31\pm4\%$) and $-0.6$ dB ($-13\pm4\%$), with the defibrillator ON and running on its internal battery or on line-power, respectively, relative to the SNR obtained with the defibrillation system shut down (OFF).

During SSFP imaging (FIG. 2B), artifacts from the Zoll Medical Stat patz pads extended only 6 mm below the volunteer's abdominal skin surface. As a result, they did not mask any important anatomy.

Swine Fibrillation and Defibrillation Experiments

All animal works were approved by the Animal Care and Use Committee (ACUC) of the Johns Hopkins University.

To assess the operation of the MRI-compatible defibrillation system, 40 kg swine models are utilized. The swine had previously inducted chronic left-ventricular infarcts. They were anesthetized and intubated. During the experiments, the swine were fibrillated using the custom fibrillation unit (n=3), and thereafter defibrillated using the modified defibrillation system, using a 200 Joule, 8 ms pulse, biphasic pulse routine.

In some embodiments, two cardiac events were induced within a conventional animal fluoroscopy suite, which tested normal (non-MRI) defibrillation functionality of the modified system. Two cardiac events were then induced inside a 1.5 Tesla Siemens 0.7 m patient-bore Aera scanner. Before the cardiac arrest, during the arrest, and during the recovery to sinus rhythm which followed defibrillation, the swine were monitored using MRI-compatible hemodynamic monitors. (Invivo Precess 3160, Gainesville, Fla.)

Figure 3B:
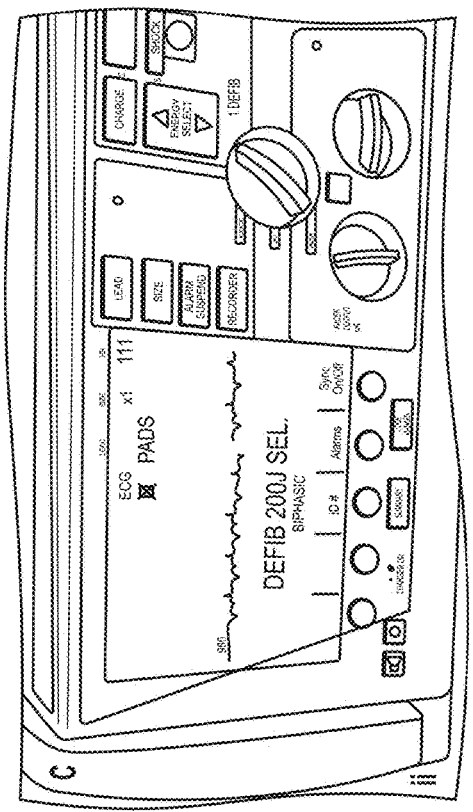
FIGS. 3A and 3B show a swine test of the MRI-compatible defibrillation system in an animal fluoroscopy lab according to an embodiment of the invention.
Figure 3B:
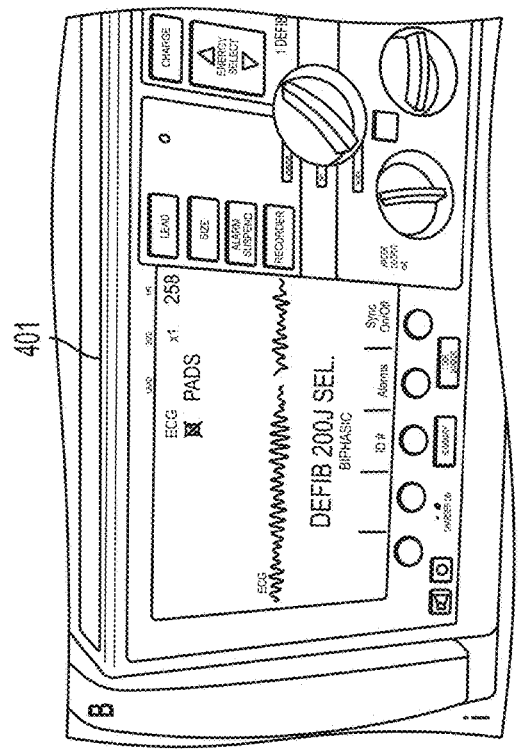
Figure 3A:
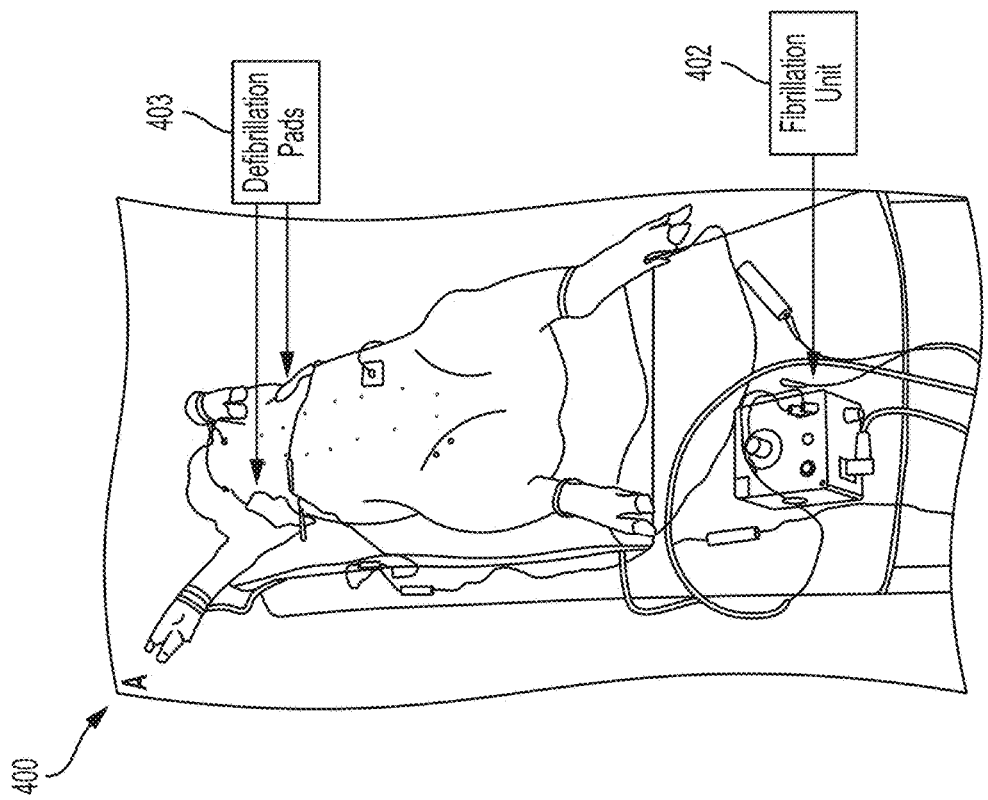

FIGS. 3A and 3B show a swine test of the MRI-compatible defibrillation system 400 in an animal fluoroscopy lab.

FIG. 3A shows the swine on the table, with arrows pointing to the location of the defibrillation pads 401 on the chest, as well as the fibrillation generator (unit) 402, which was used to induce the cardiac arrest. Image (i) in FIG. 3B shows a display of the Zoll Medical generator 403 during a Ventricular Fibrillation (VF) in a cardiac arrest. Image (ii) in FIG. 3B shows a display of the Zoll Medical generator 403 in a few seconds after defibrillation.

The modified defibrillator system's chassis (defibrillator generator and low-pass filter) was placed on a table ~1.5 m from the swine table, while the fibrillation apparatus was placed on the fluoroscopy table. Stimulation from the apparatus produced ventricular fibrillation (VF), which was reversed with either a single (n=1) or two repeated (n=1) defibrillation pulses. The Zoll Medical generator's ECG display recorded the cardiac events and recovery properly (FIG. 3B).

Swine Heating Experiments

Figure 4:
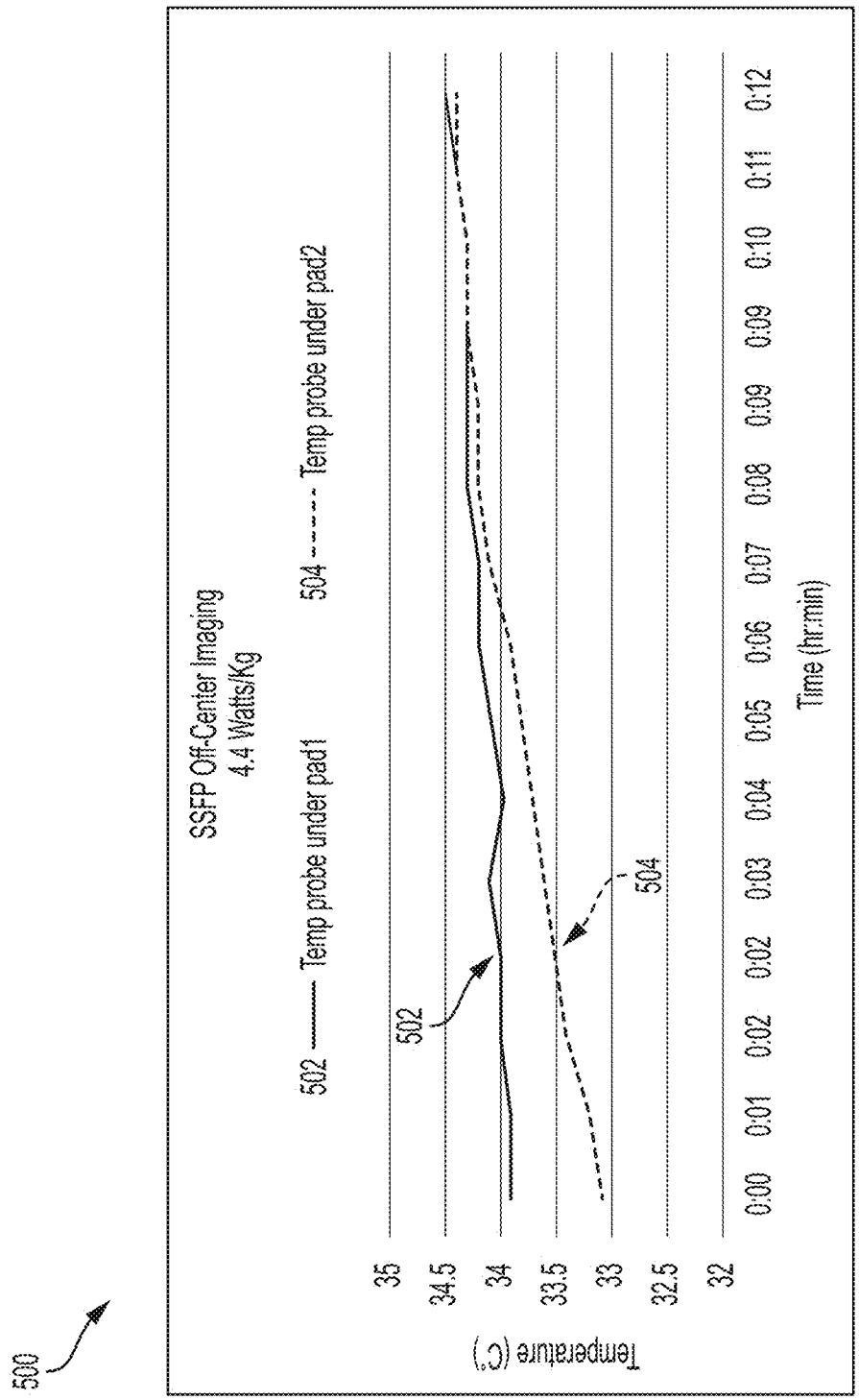
FIG. 4 shows temperatures recorded underneath the two defibrillation pads in a radio-frequency heating during imaging in a swine model according to some embodiments of the invention.

FIG. 4 shows temperatures recorded 500 underneath the two defibrillation pads in a radio-frequency heating during imaging in a swine model. The swine's head was placed at magnet iso-center and the torso moved laterally in a left-right direction, in order to maximize the electric field (from radio-frequency pulses transmitted by the MRI's body coil) which is induced onto the defibrillation pads and cables, which are found at +20 cm Superior-Inferior and +15 cm Left-Right. A steady-state free precession (SSFP) sequence with 4.4. W/kg Specific absorption rate (SAR) was used. The line 502 in FIG. 4 denotes temperatures recorded underneath the defibrillation pad 1 (between the pad 1 and the patient skin). The line 504 in FIG. 4 denotes temperatures recorded underneath the defibrillation pad 2 (between the pad 2 and the patient skin). The pad 2 leaned against the MRI bore wall (e.g. the most extreme off-center situation) and consequently demonstrated the largest temperature variation.

In FIG. 4, during the 11-minute continuous imaging experiment using the 4.4 Watt/kg SSFP sequence, and using the extremely off-center defibrillation pad localization, the peak temperature rise observed below the defibrillation pads was 1.4° C., which is within FDA guidelines. The cable temperature rise was <0.1° C. Turbo spin echo (TSE) scans at this location, as well as SSFP scans at other locations, resulted in smaller temperature increases.

Figure 5C:
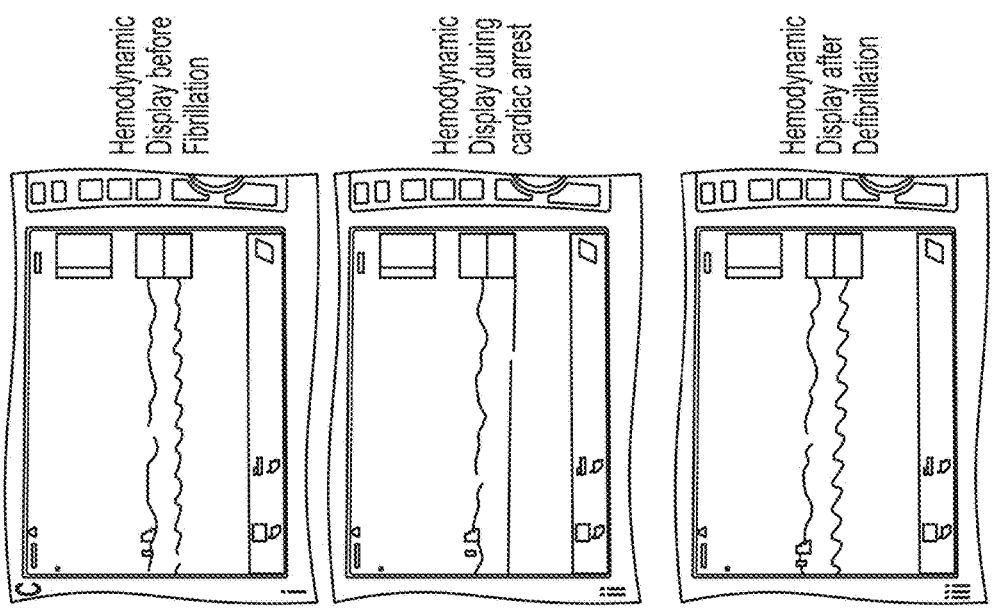
FIGS. 5A, 5B, and 5C show a swine test of the MRI-compatible defibrillation system in a 1.5 T MRI according to an embodiment of the invention.
Figure 5A:
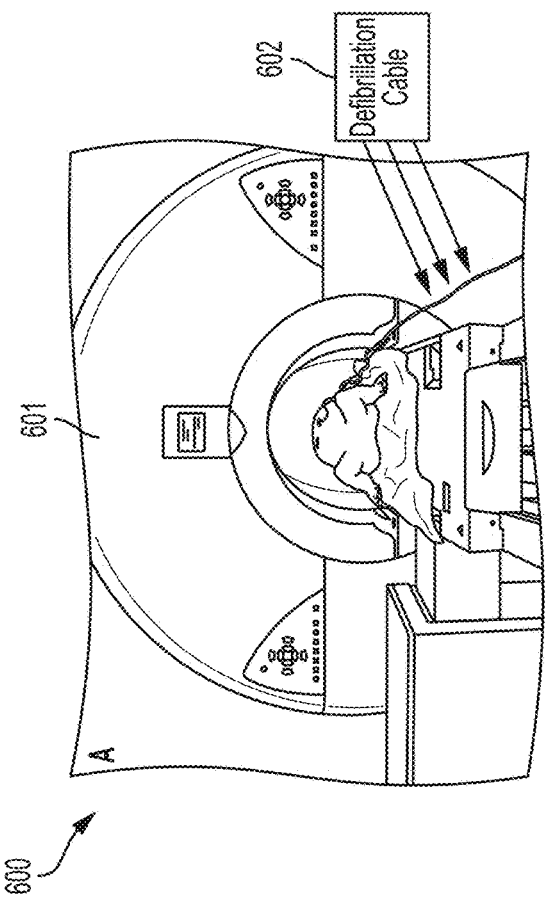
Figure 5B:
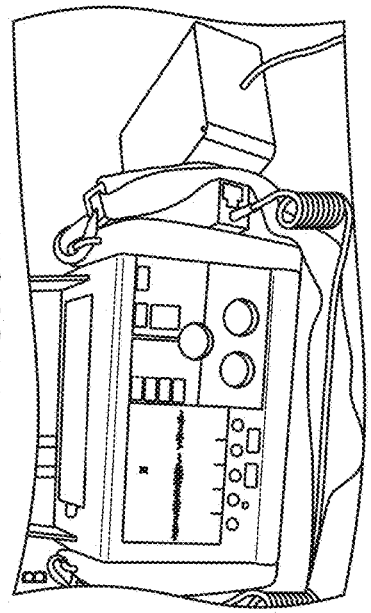

FIGS. 5A, 5B and 5C show a swine test of the MRI-compatible defibrillation system 600 in a 1.5 T MRI system. FIG. 5A shows the swine inside the MRI scanner 601, with the heavy arrows pointing to the defibrillation cables 602, as they enter the MRI scanner 601. FIG. 5B shows a display of the Zoll Medical generator during the experiment. The generator's ECG display was unreliable, due to sizeable MHD overlays on the traces. FIG. 5C shows a display of the MRI-compatible hemodynamic display. Image (i) in FIG. 5C shows a display of the MRI-compatible hemodynamic display before fibrillation. Image (ii) in FIG. 5C shows a display of the MRI-compatible hemodynamic display during a Ventricular Fibrillation (VF) in a cardiac arrest. Image (iii) in FIG. 5C shows a display in a few seconds after defibrillation. The middle trace in the image (iii) in FIG. 5C shows pulse oximetry (SPO2) value which is indicative of the state of the animal, and it is used as a surrogate to a reliable ECG trace.

During experiments performed within the MRI suite (FIG. 5A), the modified defibrillator system's chassis was placed on the right side of the MRI magnet, ~1.5 meters from the front of the MRI's gantry. At this distance, it was easy to operate the M-series generator, and there was no magnetic attraction of the chassis. Fibrillation inside the MRI scanner resulted in VF (FIG. 5B), which was reversed with a single (n=2) defibrillation pulse. The Zoll Medical generator's ECG display did not properly record the VF event, as it was obscured by Magneto-hydrodynamic (MHD)[81] overlays on the ECG trace, but this was noted properly using the MRI-compatible hemodynamic display, allowing for the timely delivery of defibrillation.

During defibrillation in the x-ray suite and inside the MRI, heavy swine torsos were elevated by ~0.10 m. This did not result in any damage to the MRI scanner or the defibrillation apparatus. The swine's elevation ("jump") during defibrillation did not damage the scanner, nor did it injure the subject. A ("wide-bore") 0.7 m patient-bore MRI for these experiments, whereas most current scanners have a 0.6 m patient-bore.

According to some embodiments, a multi-pole (such as 7 pole) Low-pass filter may be designed to filter emissions from the defibrillation generator. Novel aspects can include: (a) substantial filtering (such as by 80-90 dB) of differential mode noise at the MRI Larmor frequency; (b) withstanding the high-voltages incurred during administration of defibrillation pulses; and (c) passing the <1 MHz (such as 67-KHz) frequency used by the generator to validate that the defibrillation pads are connected to the patent.

Radio-Frequency traps tuned to the MRI Larmor frequency ("Baluns") are placed on the defibrillation cabling at regular (such as 30 cm) increments in order to reduce common-mode emission from the generator, as well as to prevent patient-skin heating from RF-energy induced by the MRI scanner's body transmit coil.

In some embodiments, slotted Defibrillator pads can be used, but they are optional. In some embodiments, slotting the pads may reduce RF eddy-currents produced in the pads during transmission of MRI energy. Performance of slotting may reduce the size of the image artifact created by these eddys on MRI images, which is particularly important in MRI sequences sensitive to such artifacts, such as steady state free precession (SSFP), as well as at higher MRI field strengths.

Figure 6A:
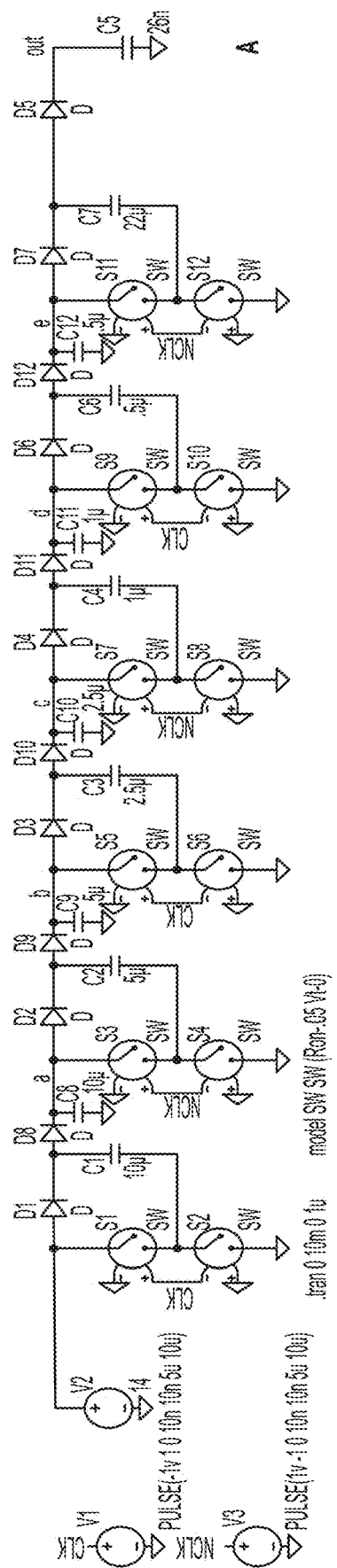
FIG. 6A shows a circuit diagrams of a single stage of the six geometrical step-up units that may be used according to some embodiments of the invention.
Figure 6B:
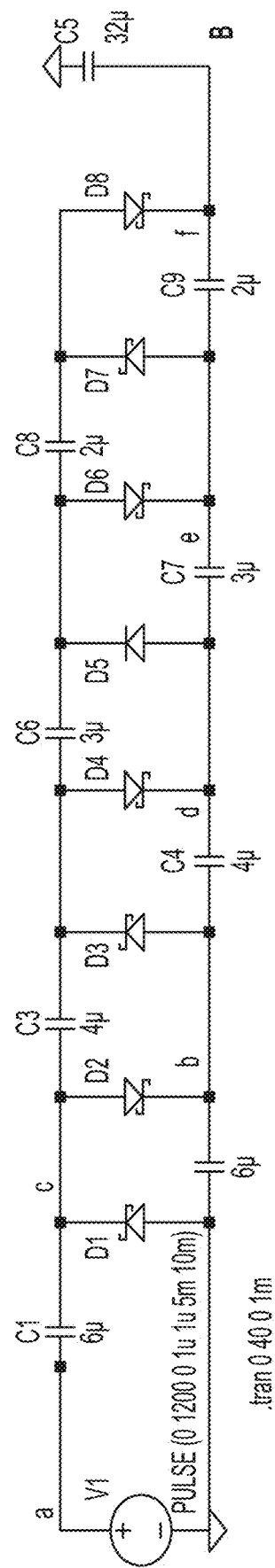
FIG. 6B shows a circuit diagram of a single stage of the high voltage multiplier circuits, which follows the geometric step-up units according to some embodiments of the invention.

In some embodiments, a non-magnetic voltage multiplier circuit may be used for stepping up the battery and/or main supply voltage to the voltage needed for defibrillation. Many types of multipliers can be used, including voltage and geometric multipliers. For example, FIG. 6A shows a circuit diagram of a single stage of the six geometrical step-up units that may be used according to some embodiments of the invention. FIG. 6B shows a circuit diagram of a single stage of the high voltage multiplier circuits, which follows the geometric step-up units according to some embodiments of the invention.

Different numbers of geometric step-up and high voltage multiplier units may be used depending on the desired output voltage and the input voltage used. In addition, a small iron based voltage transformer may be used to increase the input voltage to an intermediate level before being applied to the non-magnetic voltage multiplier units. This latter configuration may reduce the number and complexity of the non-magnetic voltage multiplier units while incorporating sufficiently small amounts of ferromagnetic material that no significant force is generated on the defibrillator generator.

In some embodiments, a signal generator and switching system (not shown) may be used to apply a waveform to the patient just prior to delivery of the defibrillator shock. This waveform is intended to condition the skeletal muscle to reduce or avoid its violent contraction which would otherwise be caused by the defibrillator shock. Such a waveform includes a ramped oscillating waveform starting at a low peak-to-peak voltage (such as 0 volts and increasing (such as linearly over time) to a peak of 10-500 volts peak to peak. The duration of the pre-shock waveform is such as 10-1000 ms, and the frequency of the oscillations is such as 100-3000 Hz. The waveform could be any oscillating waveform, but is often sinusoidal or square. In the above description, MRI-compatible defibrillators may permit the diagnosis and treatment of higher-risk patient populations within MRI scanners, significantly improving the patient-care options for these patients.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A magnetic-resonance-imaging-compatible (MRI-compatible) cardiac defibrillator, comprising:
    a defibrillator generator comprising a plurality of stages of geometric multipliers followed by a plurality stages of voltage multipliers;
    first and second electric wires, each being electrically connected to said defibrillator generator;
    first and second defibrillation pads, each being electrically connected to a respective one of said first and second electric wires; and
    a low pass filter electrically connected between said defibrillator generator and said first and second electric wires to prevent a noise in an MRI image caused by a radiofrequency interference from the defibrillator as well as protect a patient and the defibrillator from MRI radiofrequency imaging signals,
    wherein said low pass filter has a cutoff frequency set such that differential mode noise at an MRI Larmor frequency is in an attenuated band while a system-test signal by said defibrillator generator is in a pass band of said low pass filter,
    wherein said defibrillator generator is an MRI-compatible defibrillator generator that is substantially free of magnetic materials.

2. The MRI-compatible cardiac defibrillator according to claim 1, wherein said low pass filter is at least a 7-pole low pass filter constructed to filter said differential mode noise at said MRI Larmor frequency by at least 80 dB.

3. The MRI-compatible cardiac defibrillator according to claim 1, wherein said low pass filter is at least a 7-pole low pass filter constructed to filter said differential mode noise at said MRI Larmor frequency by at least 90 dB.

4. The MRI-compatible cardiac defibrillator according to claim 1, wherein said first and second electric wires are formed into a twisted pair of wires.

5. The MRI-compatible cardiac defibrillator according to claim 1, further comprising a plurality of radio-frequency (RF) traps tuned to said MRI Larmor frequency attached to said first and second electric wires spaced apart from each other in order to reduce common-mode emission from said defibrillator generator and to prevent patient-skin heating from RF-energy induced by an MRI scanner's body transmit coil.

6. The MRI-compatible cardiac defibrillator according to claim 1, wherein said defibrillation pads are slotted defibrillation pads.

7. The MRI-compatible cardiac defibrillator according to claim 1, wherein said MRI-compatible defibrillator generator comprises six stages of geometric multipliers followed by thirteen stages of voltage multipliers.

8. The MRI-compatible cardiac defibrillator according to claim 1, wherein said defibrillator generator is configured to produce a muscle-conditioning signal immediately prior to a cardiac stimulating pulse so as to decrease a degree of rapid muscle contraction by a subject undergoing cardiac defibrillation.

9. The MRI-compatible cardiac defibrillator according to claim 1, wherein said defibrillator generator is configured to apply a waveform to the patient just prior to delivery of a defibrillator shock.

10. The MRI-compatible cardiac defibrillator according to claim 9, wherein the waveform is used to condition the skeletal muscle to reduce or avoid its violent contraction caused by the defibrillator shock.

11. A kit for converting a cardiac defibrillator to an MRI-compatible cardiac defibrillator, said cardiac defibrillator comprising a defibrillator generator, and said kit comprising:
    a low pass filter structured to be electrically connected to said defibrillator generator between first and second electric wires of said MRI-compatible cardiac defibrillator to prevent a noise in an MRI image caused by a radiofrequency interference from the defibrillator as well as protect a patient and the defibrillator from MRI radiofrequency imaging signals,
    wherein said low pass filter has a cutoff frequency between a pass and attenuated bands set such that differential mode noise at an MRI Larmor frequency is in said attenuated band while a signal by said defibrillator generator for system tests is in said pass band of said low pass filter,
    wherein said defibrillator generator comprises a plurality of stages of geometric multipliers followed by a plurality stages of voltage multipliers,
    wherein said defibrillator generator is an MRI-compatible defibrillator generator that is substantially free of magnetic materials.

12. The kit according to claim 11, wherein said low pass filter is at least a 7-pole low pass filter constructed to filter said differential mode noise at said MRI Larmor frequency by at least 80 dB.

13. The kit according to claim 11, wherein said low pass filter is at least a 7-pole low pass filter constructed to filter said differential mode noise at said MRI Larmor frequency by at least 90 dB.

14. The kit according to claim 11, further comprising said first and second electric wires, said first and second electric wires being formed into a twisted pair of wires.

15. The kit according to claim 11, further comprising a plurality of radio-frequency (RF) traps tuned to said MRI Larmor frequency attached to said first and second electric wires spaced apart from each other in order to reduce common-mode emission from said defibrillator generator and to prevent patient-skin heating from RF-energy induced by an MRI scanner's body transmit coil.

16. The kit according to claim 11, further comprising slotted defibrillation pads.

\* \* \* \* \*